United States Patent
Fellay et al.

[11] Patent Number: 5,404,761
[45] Date of Patent: Apr. 11, 1995

[54] DEVICE FOR CONTINUOUSLY COLLECTING A DIALYSATE SAMPLE

[75] Inventors: Gilbert Fellay, Villars-sur-Glâne; Jean-Pierre Gabriel, Fribourg; Pierre Vuilleumier, Gletterens; Gilbert Widmer, Le Landeron, all of Switzerland

[73] Assignee: Ciposa Microtechniques S.A., Switzerland

[21] Appl. No.: 30,172

[22] PCT Filed: Jul. 17, 1992

[86] PCT No.: PCT/CH92/00150
§ 371 Date: Mar. 15, 1993
§ 102(e) Date: Mar. 15, 1993

[87] PCT Pub. No.: WO93/02346
PCT Pub. Date: Feb. 4, 1993

[30] Foreign Application Priority Data
Jul. 19, 1991 [FR] France ................. 91 09319

[51] Int. Cl.⁶ ............................................. G01N 1/18
[52] U.S. Cl. ............................. 73/863.23; 73/863.52; 73/863.61
[58] Field of Search ........... 73/863.23, 863.24, 863.25, 73/863.21, 863.31, 863.33, 863.41, 863.43, 863.52, 863.61

[56] References Cited
U.S. PATENT DOCUMENTS 3,512,418  5/1970  Broman, Jr. .
3,942,388  3/1976  Rathnow et al. .
4,153,513  5/1979  Edelmann et al. ............... 435/14
4,229,542  10/1980  Nylen et al. ..................... 435/291
4,244,787  1/1981  Klein et al. ..................... 204/153.1
4,623,450  11/1986  Vantard et al. ................. 210/87
4,963,256  10/1990  Nelson ............................ 210/232

FOREIGN PATENT DOCUMENTS 0069029  1/1983  European Pat. Off. .
0298872  1/1989  European Pat. Off. .
1181412  6/1959  France .
6602291  8/1967  Netherlands .

Primary Examiner—Tom Noland
Attorney, Agent, or Firm—Davis, Bujold & Streck

[57] ABSTRACT

A method and a device for collecting a dialysate sample for a qualitative and quantitative analysis of all the dialysate collected during replacement therapy for renal failure. In a preferred embodiment, the device (10) comprises a buffer receptacle (20) consisting of a cylindrical container on a separator (30). The separator (30) has a collecting chamber (36) with a number of calibrated ducts (39 and 42) formed at its periphery. Calibrated ducts (39) open into a flow channel (38) and the dialysate conveyed by the ducts passes into a discharge duct (34), whereas calibrated ducts (42) lead to a collector (41) communicating with a duct (35). The dialysate collected at the outlet of duct (34) is analyzed. This device allows the dialysate generated during a dialysis process to be sampled continuously and the composition of this sample represents that of all the dialysate produced.

12 Claims, 2 Drawing Sheets

DEVICE FOR CONTINUOUSLY COLLECTING A DIALYSATE SAMPLE

FIELD OF THE INVENTION

The present invention concerns a device for continuously collecting a dialysate sample for analysis, said sample being representative of the dialysate generated during the dialysis procedure with respect to both composition and volume, said device comprising a first means for separating a predetermined amount of dialysate throughout the dialysis procedure and a second means for direct evacuation of the remaining dialysate.

BACKGROUND OF THE INVENTION

To evaluate the effectiveness of dialysis and manage patient treatment, it is important to determine with some precision the mass transfer of blood in the dialysate, as well as water and various dissolved substances such as urea, and salts such as sodium, potassium and phosphates. These values are presently calculated from measurements known as "clearances" derived from the blood flow rate through the artificial kidney and from plasma concentrations at the input and output of the kidney. This involves hypotheses about the kinetics of transfers which are invalid for numerous dissolved substances. A far more reliable method, known in the art but not currently used, consists of collecting all the dialysate, that is 80 to 150 liters per session per patient, and after thoroughly homogenizing it, measuring the total volume of dialysate and measuring the concentration of dissolved elements. For this reason, the methods currently used consist of sampling the dialysate and drawing off the amount of material required for analysis. Relatively complex equipment is used for this procedure. Such an apparatus is described, for example, in U.S. Pat. No. 3,512,418, which, is theoretically designed to draw off a predetermined percentage of a liquid substance circulating through a conduit. Similar devices are described in U.S. Pat. No. 3,942,388 and French Patent No. 1.181.412.

Unfortunately, the apparatus or the devices lack precision and fail to obtain a sample of material for analysis which is an exact reflection of the total material evacuated. This is a ms, or flaw, especially in the case of analyzing dialysate evacuated by a dialysis machine. For this particular application it is essential that the sample correspond exactly to the dialysate exiting the machine so the parameters of the dialysis procedure can be precisely adjusted.

The present invention proposes a device for implementing this procedure which collects a dialysate sample that accurately represents the composition of the total dialysate and the volume of which is a known proportion of the total dialysate volume.

SUMMARY OF THE INVENTION

To achieve this the device according to the invention is characterized in that it has a buffer receptacle through which all the dialysate flows, said receptacle being associated with a separator provided with said first means and said second means.

According to a preferred embodiment the separator is attached to the base of the buffer receptacle and said first means and said second means are designed so that the free level of liquid in the receptacle is always situated above the upper level of the separator.

Said first means advantageously comprises at least one calibrated duct and said second means comprises a series of calibrated ducts, with all the calibrated ducts being identical and located at the same height in relation to the free surface of liquid in the buffer receptacle.

The calibrated ducts are preferably radially disposed and spaced regularly on a circular portion centered on the axis of the buffer receptacle.

In a particularly advantageous arrangement the calibrated ducts are designed to allow communication between a collecting chamber, which is formed in the base of the buffer receptacle and communicates with it, and a flow channel.

According to this embodiment the flow channel is designed to communicate with an outflow of liquid through a funnel and the level of liquid in the flow channel is lower than the calibrated ducts.

The calibrated duct is preferably designed to allow communication between a collection chamber formed in the base of the buffer receptacle and a collector.

The collector is preferably provided with an outflow and the level of liquid in the collector is lower than the calibrated duct.

According to one design which is particularly advantageous because of its compact size, the separator comprises a central cone, the peak of which is located on the axis of the buffer receptacle, and the base of which is situated near the calibrated ducts and partially defines the collection chamber.

The buffer receptacle preferably comprises a liquid intake opening essentially equal in size to the sum of the outflow sections so that the flow rate at the entrance to the buffer receptacle is essentially equal to the total flow rate at the output of the device and the level in the receptacle remains fairly constant.

The input opening preferably opens into the buffer receptacle through a group of channels which are arranged in a radial design around the opening.

BRIEF DESCRIPTION OF THE DRAWINGS

The present invention will be better understood with reference to the description of one embodiment and to the attached drawing, in which.

DESCRIPTION OF THE PREFERRED EMBODIMENT

Figure 1:
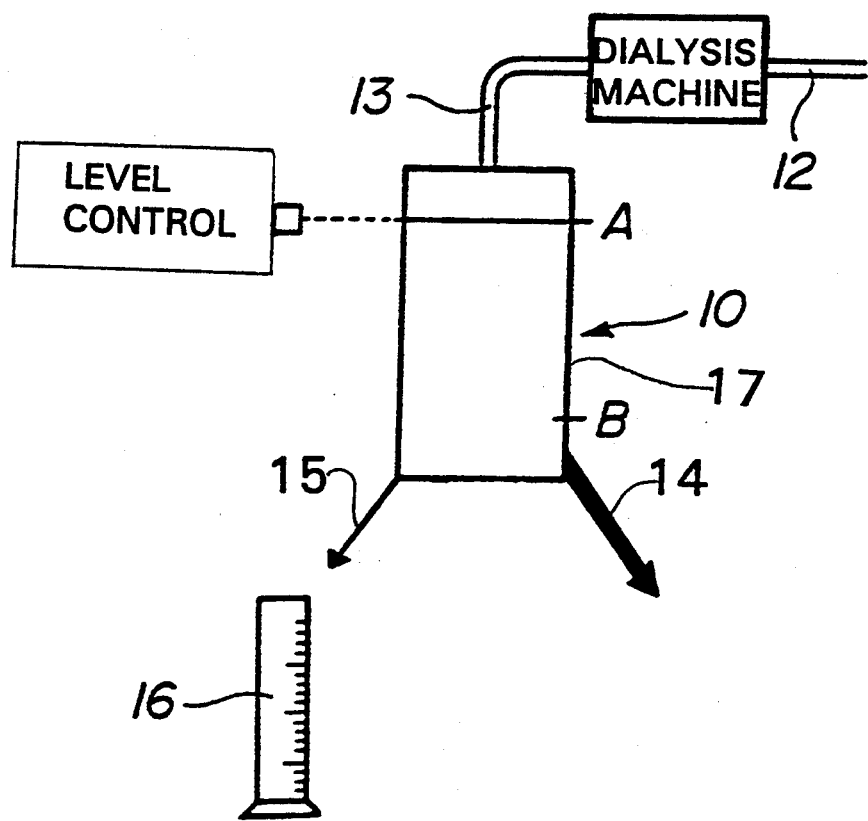
FIG. 1 is a schematic view showing the principle which inspired the method of the invention.

With reference to FIG. 1 the device 10 for collecting a dialysate sample for analysis is connected to the output of a dialysis machine 11 receiving a base solution directed through a duct 12 and discharges a dialysate which is directed through duct 13 toward device 10. It is important for the doctor to know the flew rate and composition of the initial dialysate and also the composition and flow rate of the final dialysate. Since, practically speaking, the volume in question is too large to be systematically collected in its totality in a clinical setting, device 10 separates the dialysate into two streams 14 and 15, respectively, which have exactly the same composition. Stream 15 is collected in an appropriate receptacle 16 for analysis while stream 14 is directly drained off. Since the composition of the two streams is identical and the flow ratio is known, precise analysis of the liquid collected in receptacle 16 provides the data the doctor needs in order to determine the parameters for a course of treatment.

Device 10 consists of a buffer receptacle 17 for collecting dialysate at the output of the dialysis machine 11 before allowing it to flow freely toward the separator per se which separates the two streams 14 and 15. It is imperative that buffer receptacle 17 be constantly supplied and that the level of liquid therein be high enough for the separator to function correctly. To achieve this there is advantageously provided a level control element 18 which maintains the liquid level on level mark A or in an area between two level marks A and B. In practice the ducts which define streams 14 and 15 are calibrated so that the volume of dialysate collected in the buffer receptacle corresponds essentially to the volume of dialysate evacuated so that the level automatically remains constant. When the level in the receptacle is elevated pressure in the evacuation zone increases and the flow rate increases, and as a result the level readjusts. Thus the level is, in effect, self-regulating.

Figures 2, 3:
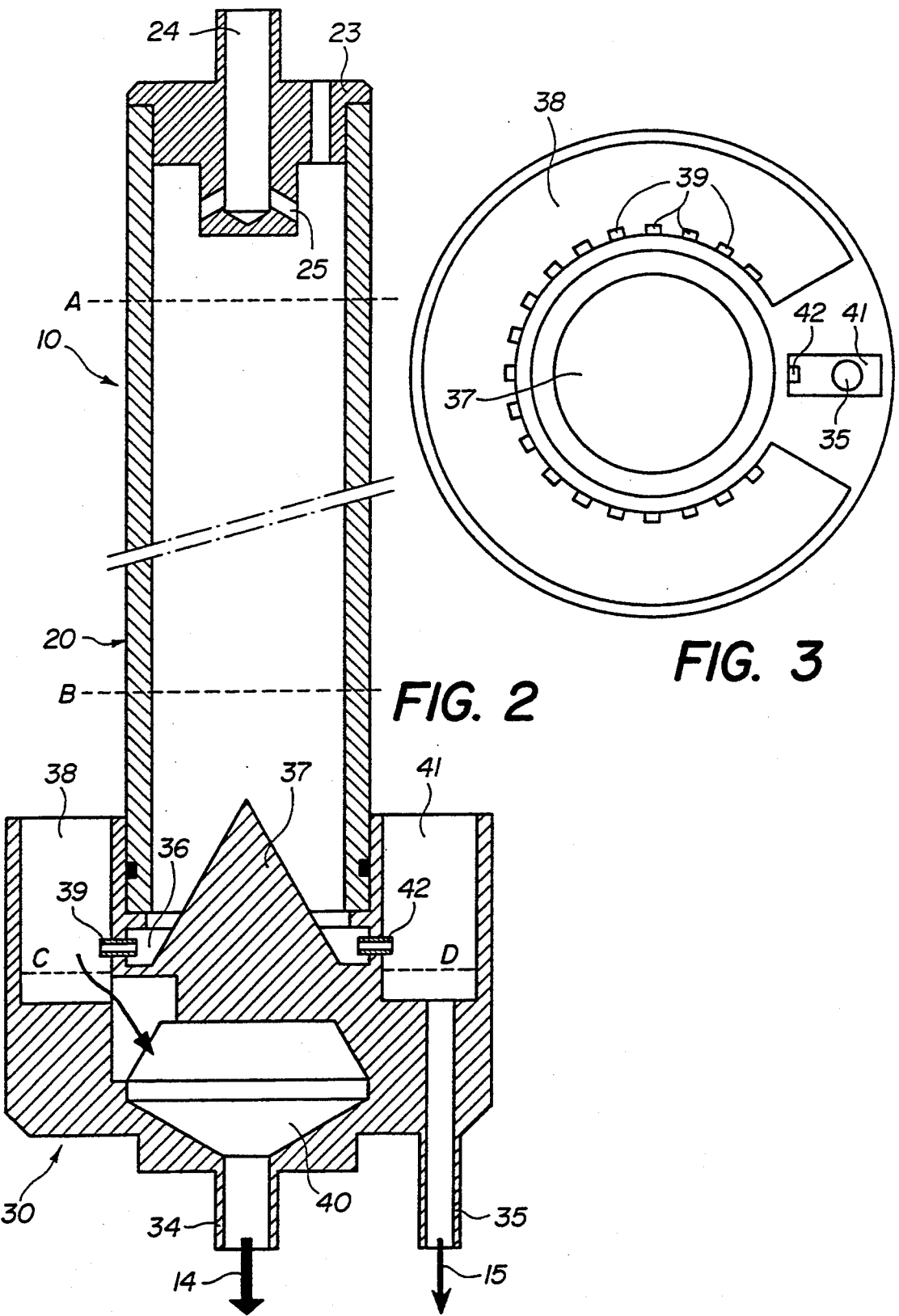
FIG. 2 is a longitudinal cross-section of one preferred embodiment of the device according to the invention.
FIG. 3 is a plane view of the device according to the invention.

FIG. 2 shows a preferred embodiment of device 10. In this embodiment buffer receptacle 20 is generally cylindrical and has a stopper 23 at its upper end with an opening 24 where duct 13 (defined in FIG. 1) terminates. This opening 24 communicates with the inside of the buffer receptacle 20 by at least one channel 25 and preferably a group of channels 25 distributed regularly around opening 24.

Separator 30 consists of a block attached to the lower end of the buffer receptacle and comprising two outflows 34 and 35 corresponding to streams 14 and 15 respectively. For this purpose the separator comprises a collection chamber 36 disposed in the upper portion, which is annular in shape and coaxially surrounds a distributor cone 37. This collection chamber communicates with an at least partially annular flow channel 38 by means of a certain number of calibrated conduits 39. The dialysate flowing through this flow channel 38 is collected by a funnel 40 and ultimately is evacuated through conduit 34. In addition, collection chamber 36 communicates with a collector 41 by means of at least one calibrated conduit 42. The dialysate collected in collector 41 is directed through conduit 35 to the analysis receptacle 16.

As the plane view in FIG. 3 shows, calibrated conduits 39 and 42 are all identical. In the embodiment shown, conduits 39 communicating with flow channel 38 are nineteen in number and there is only one conduit 42 communicating with receptacle 41. However, this ratio could be different and the number of conduits 39 and 42 could be modified in other embodiments. In this embodiment 1/20th of the dialysate volume is collected for analysis. Dialysate sampling takes place continuously so that at any given moment the composition of the collected dialysate corresponding to stream 15 is identical to that of the evacuated dialysate corresponding to stream 14.

It is particularly important for the opening of the device to be free and for the upper level of liquid in the buffer receptacle to be free. Furthermore, all ducts 39 and 42 must be identical and must open into the evacuation chambers consisting of funnel 40 on the one hand and collector 41 on the other hand, where the liquid also has a free surface C and D respectively. For this reason nothing interferes with the free flow of streams 14 and 15. Pressure upstream of conduits 39 and 42 is absolutely identical because it is created by the column of liquid in the buffer receptacle. Variations in level cause the same pressure variations in all the conduits.

Since the conduit outputs are free, the divider does not generate any counter-pressure on the upper portion of the apparatus.

In sum, the design of this device is simple and precise. It is easy to calibrate because all the conduits are identical. The star shape allows it to be compact and facilitates separating the streams at the conduit outputs.

The present invention is not limited to the embodiments described but may undergo various modifications and assume various forms obvious to one skilled in the art. In particular, according to another variation, the first separator means may comprise at least one measuring pump, for example a peristaltic pump, which is intermittently activated perhaps every ten seconds.

We claim:

1. Device for continuously collecting a dialysate sample for analysis, said sample being representative with respect to both composition and volume of the composition and the volume of the totality of dialysate generated in the course of a dialysis procedure, said device comprising a first means for separating a predetermined proportion of dialysate throughout the dialysis procedure, and a second means for directly evacuating the remainder of the dialysate, said device comprising a buffer receptacle (20) through which all the dialysate passes, said buffer receptacle being associated with a separator (30) having said first means and said second means.

2. Device according to claim 1 wherein the separator (30) is attached to a base of the buffer receptacle and said first means and said second means are designed so that free liquid in the buffer receptacle is at a level constantly higher than an upper level of the separator.

3. Device for continuously collecting a dialysate sample for analysis, said sample being representative with respect to both composition and volume of the composition and the volume of the totality of dialysate generated in the course of a dialysis procedure, said device comprising a first means for separating a predetermined proportion of dialysate throughout the dialysis procedure, and a second means for directly evacuating the remainder of the dialysate, said device comprising a buffer receptacle (20) through which all the dialysate passes, said buffer receptacle being associated with a separator (30) having said first means and said second means, wherein the separator (30) is attached to a base of the buffer receptacle and said first means and said second means are designed so that free liquid in the buffer receptacle is at a level constantly higher than an upper level of the separator, and wherein said first means comprises at least one calibrated duct (42) and said second means comprises a series of calibrated ducts (39), and in that said calibrated ducts are all identical and are situated at the same height in relation to the free surface of liquid in the buffer receptacle.

4. Device according to claim 3 wherein the calibrated ducts (39) are radially disposed and regularly spaced on a circular portion centered on a central axis of the buffer receptacle.

5. Device according to claim 3 wherein the series of calibrated ducts (39) allow communication between a collection chamber (36) formed in the base of the buffer receptacle and a peripheral flow channel (38) formed in the separator.

6. Device according to claim 5 wherein the flow channel (38) communicates with an outflow (34) by means of a funnel (40) and the level (C) of liquid in the flow channel is located below the calibrated ducts (39).

7. Device according to claim 5 wherein the separator comprises a central cone, the peak of which is located on a central axis of the buffer receptacle and the base of which is situated near the calibrated conduits (39, 42) and partially defines said collection chamber (36).

8. Device according to claim 3 wherein the at least one calibrated duct (42) allows communication between a collection chamber (36) formed in the base of the buffer receptacle and a collector channel (41) formed in the separator.

9. Device according to claim 8 wherein the collector channel (41) is provided with an outflow (35) and in that the level (D) of liquid in the collector channel (41) is lower than the level of the at least one calibrated duct (42).

10. Device according to claim 3, wherein the series of calibrated ducts (39) allow communication between a collection chamber (36) formed in the base of the buffer receptacle and a peripheral flow channel (38) formed in the separator,
wherein the flow channel (38) communicates with an outflow (34) by means of a funnel (40) and that the level (C) of liquid in the peripheral flow channel is located below the calibrated ducts (39),
wherein the at least one calibrated duct (42) allows communication between said collection chamber (36) and a collector channel (41) formed in the separator,
wherein the collector channel (41) is provided with an outflow (35) and in that the level (D) of liquid in the collector channel (41) is lower than the level of the at least one calibrated duct (42).

11. Device according to claim 10 wherein the buffer receptacle (20) comprises an inlet opening (24) for liquid which is essentially equal in section to the sum of the sections of the outflows (34, 35) so that the flow rate of liquid coming into the buffer receptacle is essentially equal to the total flow rate at the output of the device and that the level (A) in this receptacle remains generally constant.

12. Device according to claim 11 wherein the inlet opening (24) opens into the buffer receptacle through a group of channels (25) which are generally radially disposed in relation to said opening.

* * * * *